United States Patent [19]
Spitler et al.

[11] 3,991,182
[45] Nov. 9, 1976

[54] TRANSFER FACTOR

[75] Inventors: Lynn E. Spitler, Tiburon; Alan S. Levin, San Francisco; H. Hugh Fudenberg, Mill Valley; Daniel P. Stites, Palo Alto, all of Calif.

[73] Assignee: The Regents of the University of California, Berkeley, Calif.

[22] Filed: Nov. 8, 1973

[21] Appl. No.: 413,927

Related U.S. Application Data

[63] Continuation-in-part of Ser. No. 190,670, Oct. 19, 1971, abandoned.

[52] U.S. Cl. .............................................. 424/101
[51] Int. Cl.$^2$........................................ A61K 35/14
[58] Field of Search ................................... 424/101

[56] References Cited

OTHER PUBLICATIONS

Lawrence et al., Mediators of Cellular Immunity, Academic Press, N.Y., (1969) pp. 177–181.

*Primary Examiner*—Sam Rosen
*Attorney, Agent, or Firm*—Phillips, Moore, Weissenberger, Lempio & Strabala

[57] ABSTRACT

A method of treating human patients suffering from immune deficiency diseases by extracting a "transfer factor" from leucocytes obtained from healthy donors who exhibit immune response to said diseases and injecting said "transfer factor" into said diseased patients to thereby suppress disease symptoms.

7 Claims, No Drawings

TRANSFER FACTOR

The invention described herein was made during the performance of work under research grants from the United States Public Health Service.

BACKGROUND OF THE INVENTION

This application is a continuation-in-part of our application Ser. No. 190,670, filed Oct. 19, 1971, now abandoned.

The present invention relates to utilization of massive dosage units of leucocyte extract for the relief of symtoms associated with diseases due to familial defects in cellular immunity and represent a transfer in immunity in man. Diseases associated with defects in cellular immunity include the Wiskott-Aldrich syndrome, Swiss type agammaglobulinemia, and mucocutaneous candidiasis. A common feature of all these conditions is a condition in which failure of development of thymus-lymphocytes results in a failure to show delayed type hypersensitivity. The conditions may be classified as congenital sex-linked immune deficiencies, such as the Wiskott-Aldrich syndrome, selective cellular immune deficiencies, such as mucocutaneous candidiasis, or acquired cellular immune deficiencies.

A survey of conditions linked to specific failures of immunity is set out in *Immunology*, J. H. Humphfrey and R. G. White, 1970, F. A. Davis Company, pages 324–347. Examplary of conditions responsive to treatment with the leucocyte extract of this invention is the Wiskott-Aldrich syndrome noted as a sex-linked recessive disease characterized by recurrent pyogenic infections, eczma, and thrombocytopenia. Subjects with this syndrome have lymphopenia, lack delayed hypersensitivity as assayed by skin tests, and have defective lymphocyte blastogenesis.

The utilization of leucocyte extracts in small amounts for indicating a delayed-type hypersensitivity in healthy recipients was undertaken prior to the method disclosed herein, and this effect has been termed "transfer factor" by the originator, H. S. Lawrence. His work in this field has been summarized in:

Lawrence, H. S., *Advan. Immunol.*, 11, 196 (1969);
Lawrence, H. S., *Mediators of Cellular Immunity*, eds., H. S. Lawrence and M. Landy (New York: Academic Press, 1969).

The Lawrence work, however, was directed towards skin tests in healthy patients and utilized only enough transfer factor to transfer skin test reactivity to the recipient. The cell dosage utilized in the Lawrence technique is in the order of $85 \times 10^6$ white cells as in the transfer of tuberculin sensitivity [confer *Advan. Immunol.*, 11, 203 (1969] and in the Lawrence technique the recipient is tested a day later and produces a typical delayed-type reaction. A summary of the Lawrence work for producing transfer factor is given at page 539 of Humphrey and White text noted above.

The present invention differs from the Lawrence technique in that Lawrence used healthy recipients and low doses of transfer factor for the purpose of demonstrating the transfer in skin activity. On the other hand, this present invention initiates the concept of the use of massive doses of transfer factor in the order of the amount prepared from $7.5 \times 10^8$ to $6.0 \times 10^9$ leucocytes in subjects exhibiting disease symptoms deriving from defects in cellular immunity for the purpose of reconstituting the cellular immunity and giving relief from symptoms. Some additional differences of technique in the preparation of the leucocyte extract or transfer factor may be illustrated as follows:

|  | Present Method | H. S. Lawrence Method |
|---|---|---|
| Anticoagulant for Blood | EDTA | Heparin or cation exchange resins |
| Method of Handling Blood | Sediment in syringe, express into centrifuge tubes, spin, wash | Put blood in potato tubes, add fibrinogen, pipette in 10 ml aliquots into centrifuge tubes, sediment, pipette into Lawrence tubes, spin. OR Sediment in Fenwall bag, siphon off red blood cells, siphon WBC-plasma, layer into Lawrence tubes, centrifuge, pool. |
| Dialysis | Ratio of dialyzant to dialyzate = 1:500. Dialysis performed against distilled water. | Ratio of dialyzant to dialyzate = 1:1. Dialysis usually performed against saline, sometimes against distilled water. |

It is of further note that the transfer factor prepared according to Lawrence is "heat labile", while transfer factor prepared according to the present invention is "heat stable". In addition analysis of the transfer factor prepared according to the present invention indicates a mean molecular weight of less than 20,000 for the transfer factor disclosed herein, while the transfer factor disclosed by Lawrence had weights generally above this range.

In the present invention the healthy donor is selected with the viewpoint of transferring immunity to a recipient suffering present symptoms from a disease. The leucocyte extract is prepared according to the generalized chart above, the article A. S. Levin, L. E. Spitler, D. P. Stites, and H. H. Fudenberg, *Proc. NAS*, 67, No. 2, pp. 821–828, Oct. 1970, and the illustrative example which follows.

With respect to the cell dosages, the previous calculation of Lawrence that $85 \times 10^6$ cells is equivalent to 0.1 ml of packed leucocytes is given at pages 202–203 of the article in *Advances in Immunology* cited above and is used herein. The present dosages utilized as for Wiskott-Aldrich syndrome effectively range from $7.5 \times 10^8$ white cells to $1 \times 10^9$, and it is noted that Lawrence's dosage is about $.85 \times 10^8$. A regimen for dosage schedule may be either of the one-shot variety or a serial dose repeated after a test and 10-day period.

In addition to the prior art attributed to Dr. H. S. Lawrence, the following articles attributed to the present research team are of interest:

A. S. Levin, L. E. Spitler, D. P. Stites, and H. H. Fudenberg, *Proc. NAS*, 67, No. 2, pp. 821–828, October 1970.

A. S. Levin, L. E. Spitler, D. P. Stites, and
H. H. Fudenberg, J. Clin. Invest., 50:59a, No. 6, June 1971.

In the past, cellular immune deficiency diseases, such as the Wiskott-Aldrich syndrome, have been treated by the technique of bone-marrow transplantation, as in F. H. Bach, R. J. Albertini, J. L. Anderson, P. Joo, and M. M. Bortin, Lancet, ii, 1364 (1968). However, this method introduced the hazard of graft-versus-host reaction and also was limited by the necessity for immunosuppression in an already compromised host. In contrast, the present method of therapy using leucocyte extracts carries neither of these limitations. Transfer factor does not contain viable cells capable of producing a graft-versus-host reaction. It is not in itself immunogenic, and it contains no hisocompatibility antigens. As first demonstrated by Lawrence, the passive transfer of delayed hypersensitivity to specific antigens by dialysates of sensitive leukocytes (transfer factor), as measured by skin tests, utilizes an active moiety which is dialyzable, heat labile, and resists freezing or treatment with DNase, RNase, or trypsin, has a molecular weight under 10,000, and contains adenine, guanine, cytosine, uracil, and ribose phosphate in polynucleotide material with possible small polypeptides. The modus of transfer factor is as yet unclear, although its potency has been demonstrated. The transfer of cellular immunity was reflected by positive skin tests in recipients as well as absence of infection, reduction in spleen size, an increase in platelet and white cell counts. Analogous to other types of treatment, the improvement in lesions is similar to subjects with other types of immune disorders treated with other means.

The contrast between the present technique and that of the previous low dosage transfer factor is set out by comparison in discussion of the previous technique in E. A. Kabat, *Structural Concepts in Immunology and Immunochemistry*, Holt, Rinehart and Winston, 1968, pages 265–270, in the discussion relating to delayed hypersensitivity transfer.

The mode of application of the transfer factor to the recipient is by subcutaneous injection (subcut) and corelative is the fact that the maladies related are diseases associated with cutaneous anergy.

In the case of the Wiskott-Aldrich syndrome, it has been noted that the symptoms of infectious eczema, splenomegaly, and leymphadenopathy treated with the present massive leucocyte extract dosages afforded significant relief.

EXAMPLE 1

Preparation of Transfer Factor

Migration inhibitory factor was assayed by the technique of R. E. Rocklin, O. L. Meyers, and J. R. David, *J. Immunol.*, 104, 95 (1970). Each supernatant was tested twice.

Lymphocyte stimulation was measured by a slight modification of the procedure described by S. D. Douglas, R. Kamin, and H. H. Fudenberg, J. Immunol., 103, 1185 (1969). Results are expressed as the ratio of the mean of triplicate experimental tubes, containing antigen or mitogen, to triplicate control cultures.

Blood (450 ml) was drawn from a normal adult male volunteer selected because his skin tests were strongly reactive to Streptokinase-Streptodornase, PPD, candida, and mumps but not reactive to coccidolin or trichophytin. These marked skin test reactions could be used to establish specificity of positive transfer.

The blood was drawn into 50-ml syringes containing sodium EDTA and 10% dextran (Macrodex 6%, Pharmacia Laboratories), mixed thoroughly, placed upright, and allowed to sediment for 2 hr. The plasma buffy-coat layer was collected, pooled, and centrifuged at 1000 rpm for 10 min at 4° C, to give a total volume of 1.6 ml of packed cells and a total cell count of 1500 $\times 10^6$. The cells were resuspended in 4 ml of pyrogen-free saline and alternately frozen and thawed 10 times, using an acetone-dry ice mixture and a 37° C water bath. Magnesium and DNase (Worthington Biochemical) were added, and the mixture was incubated at 37° C for 30 min. The resultant cell lysate was dialyzed against 500 ml of distilled water in the cold for 2 days, and redialyzed by the same procedure. The dialysate (transfer factor) was lyophilized and stored at −20° C until use, when it was dissolved in 2 ml of distilled water at room temperature and passed through a 0.45 μm Millipore filter.

1 ml of the transfer factor preparation, representing leukocyte extract obtained from $7.5 \times 10^8$ white cells, was injected subcutaneously into the deltoid area of the patient; another 0.1 ml was injected intradermally in the forearm to test for local transfer.

Clinical Testing of Transfer Factor

In investigating the ability of transfer factor to alleviate symptoms in various types of cellular immunity deficiency diseases, continuing clinical investigations are being undertaken. While not all patients in each disease category have responded positively to the administration of transfer factor, a significant number have done so. Diseases in which transfer factor has been effective in prophylaxis against infections or in therapy include the Wiskott-Aldrich syndrome, severe combined immunodeficiency disease, mucocutaneous candidiasis, chronic active hepatitis, coccidiodmycosis, dysgammaglolublinemia, Behcets' disease, apphthous stomatitis, linear morphea, familial keratoacanthoma and other immuno deficiency diseases.

In an early test (Procedures of the National Academy of Science 67:821 – 828, 1970) one patient with the Wiskott-Aldrich sydrome was treated with large doses of transfer factor. The patient showed striking clinical improvement in that he became free of infections, his eczema cleared, and his splenomegaly regressed, and new hair growth began in previous areas of alopecia. His skin tests became positive, concordant with those of the transfer factor donor, and his lymphocytes acquired the ability produce migration inhibitory factor (MIF) in response to antigenic stimulation although they remained unable to increase synthesis of DNA in response to the same antigen.

As a result of this success an additional study was carried out in which 24 patients with Wiskott-Aldrich syndrome were given transfer factor therapy. Of the 24 patients, 12 showed clinical improvement. Clinical improvement was measured by freedom from infections, clearing of eczema and regression of splenomegaly. In addition some patients have been under treatment for too brief a period at the time of this writing to be able to judge clinical change. Some patients did not exhibit improvement and the course of the disease progressed unchecked. In certain cases, patients that exhibited clinical improvement initially, later developed new symptoms or other diseases and these patients were lost.

Almost all (11) of the patients who showed clinical improvement exhibited skin reactivity after therapy whereas, before, this test had been negative. Similarly these patients also produced migration inhibitory factor (MIF) in response to antigenic stimulation, though these same patients had been unable to do so before therapy.

Transfer factor therapy as a controlled experiment was also undertaken on seven patients with combined immunodeficiency diseases (CID), although transfer factor was not expected to have an effect on this condition. However, of the seven patients treated with transfer factor, four showed conversion of skin reactivity, and two showed clinical improvement. One of these patients was kept in an isolette during the first months of his life. After he was removed from the isolette, he developed disseminated infection with herpes simplex. The lesions continued to progress despite the administration of cytosine arabinoside, but following the administration of transfer factor no further lesions developed and the patient showed dramatic improvement.

One patient with mucocutaneous candidiasis had previous courses of therapy with Amphotericin B, but always experienced a recurrence of skin lesions within a week of cessation of therapy.

No change was noted in his condition following the administration of 2 doses of transfer factor, but following the further administration of Amphotericin B and 2 units of transfer factor given simultaneously, the lesions cleared, and the patient remained free of infection for 6 months.

Of ten patients with mucocutaneous candidiasis, four showed positive clinical improvement and all of these patients showed conversion of skin test reactivity.

Transfer factor therapy has been investigated in a number of diseases of infectious etiology. Of three patients with disseminated coccidioidomycosis treated with transfer factor, one showed a dramatic response. Following the administration of transfer factor there was closure of a fistula which extended from the buttocks to the trachea. This fistula had persisted despite systemic and local antifungal therapy.

Two patients with "dysgammaglobulinemia" were treated and both showed conversion of skin test reactivity whereas only one showed clinical benefit. One patient with Bechet's disease showed dramatic clinical improvement. Her skin and lymphocyte stimulation were positive with various antigens even before the administration of transfer factor, so any change in these tests could not be evaluated.

One patient with linear morphea was treated with transfer factor from a donor who had experienced a spontaneous regression of linear morphea. The patient showed clinical improvement manifested by increased mobility of the skin, new hair growth of the involved areas, and the growth of a new fingernail previously lost due to the disease. This patient was somewhat unusual in that before therapy, she was anergic, and her lympocytes did not respond to routine antigens by proliferation of MIF production. After therapy with transfer factor she showed reactivity by all three measures of cellular immunity.

Two patients with familial keratoacanthoma showed improvement in their lesions.

The embodiments of the invention in which an exclusive property or privilege is claimed are defined as follows:

1. A method of alleviating symptoms of cellular immune deficiency diseases in a diseased man comprising administering a heat stable leucocyte extract transfer factor obtained by drawing a blood sample containing at least $7.5 \times 10^8$ white cells from a sensitive donor, adding an EDTA type anticoagulant, separating said white cells from the blood sample, suspending said white cells in saline solution and alternately freezing and thawing said suspension, thereafter lysing the suspension by incubation in the presence of magnesium and DNase, dialyzing the lysate against distilled water, separating the dialysate and lyophilizing the same, reconstituting the lyophilized product with distilled water, passing the product through a millipore filter and thereafter injecting a dosage amount of the product representing leukocyte extract obtained from at least $7.5 \times 10^8$ white cells into said diseased man and transferring immunity and delayed hypersensitivity to said diseased man.

2. The method of claim 1 wherein the extract administered is obtained from about $7.5 \times 10^8$ to $6 \times 10^9$ white cells.

3. The method of claim 1 wherein the extract is administered serially.

4. The method of claim 1 wherein the transfer factor is heat stable, has a mean molecular weight of less than 20,000 and is obtained from the blood of a healthy donor.

5. The method of claim 4 wherein said leucocytes are incubated with magnesium and DNase during the lysing process.

6. The method of claim 4 wherein the lysate is dialysed against distilled water in a ratio of about 1:500.

7. The method of claim 4 wherein the dialysate is passed through an ultra fine filter prior to injection into the patient.

* * * * *